United States Patent [19]

Radin et al.

[11] Patent Number: 5,041,441

[45] Date of Patent: Aug. 20, 1991

[54] METHOD OF CHEMOTHERAPY USING 1-PHENYL-2-DECANOYLAMINO-3-MORPHOLINO-1-PROPANOL

[75] Inventors: Norman S. Radin, Ann Arbor, Mich.; Jin-ichi Inokuchi, Imajuku, Japan

[73] Assignee: The Regents of the University of Michigan, Ann Arbor, Mich.

[21] Appl. No.: 176,920

[22] Filed: Apr. 4, 1988

[51] Int. Cl.$^5$ ............................................. A61K 31/535
[52] U.S. Cl. .................................................. 514/237.8
[58] Field of Search ...................................... 514/237.8

[56] References Cited

PUBLICATIONS

J. Inokuchi, I. Mason, and N. S. Radin, "Antitumor Activity Via Inhibition of Glycosphingolipid Biosynthesis", *Cancer Letters*, vol. 38, pp. 23–30, 1987.

J. Inokuchi and N. S. Radin, "Preparation of the Active Isomer of 1-Phenyl-2-Decanoylamino-3-Morpholino-1-Propanol, Inhibitor of Murine Glucocerebroside Synthetase", *J. of Lipid Res.*, vol. 28, pp. 565–571, 1987.

F. Felding-Haberman, K. Handa, S. Hakomori and N. Radin, "Modulation of Lymphocyte Response and IL-2-Dependent T Cell Proliferation by Gangliosides and their Derivatives and by Inhibitor of Ceramide Glycosylation", (abstract form), *FASB Journal*, vol. 2, p. A876, 1987.

S. Hakomori, "Glycosphingolipids", *Scientific American*, vol. 254, pp. 44–53, 1986.

K. S. Sundaram and M. Lev, "Inhibition of Sphingolipid Synthesis by Cycloserine In Vitro, and In Vivo;," *J. of Neurochem.*, vol. 42, pp. 577–581, 1984.

R. R. Vunnam and N. S. Radin, "Analogs of Ceramide that Inhibit Glucocerbroside Synthetase in Mouse Brain", *Chem. Phys. of Lipids*, vol. 26, pp. 265–278, 1980.

R. R. Vunnam, D. Bond, R. A. Schatz, N. S. Radin and N. Narasimhachari, "A New Class of Monoamine Oxidase Inhibitors", *J. of Neurochem.*, vol. 34, No. 2, pp. 410–416, 1980.

N. S. Radin and R. R. Vunnam, "Inhibitors of Cerebroside Metabolism", *Methods of Enzymology*, vol. 72, pp. 673–684, 1981.

K. R. Warren, R. S. Misra, R. C. Arora and N. S. Radin, "Glycosyltransferases of Rat Brain that Make Cerebrosides: Substrate Specificity, Inhibitors, and Abnormal Products", *J. of Neurochem.*, vol. 26, pp. 1063–1072, 1976.

A. V. Hospattankar, R. R. Vunnam and N. S. Radin, "Changes in Liver Lipids after Administration of 2-Decanoylamino-3-Morpholinopropiophenone and Chlorpromazine", *Lipids*, vol. 17, No. 8, pp. 538–542, 1982.

S. C. Datta and N. S. Radin, "Glucosylceramide and the Level of the Glucosidase Stimulating Proteins", *Lipids*, vol. 21, No. 11, pp. 702–709, 1980.

Y. Shoenfeld, S. Berliner, J. Pinkhas and E. Beutler, "The Association of Gaucher's Disease and Dysproteinemias", *Clin. Rev.*, vol. 64, pp. 241–243, 1980.

P. W. Pratt, S. Estren and S. Kochwa, "Immunoglobulin Abnormalities in Gaucher's Disease: Report of 16 Cases", *Blood*, vol. 31, No. 5, pp. 633–640, 1968.

Radin et al., *Biochem. Pharmacol.*, 37:2879-2886 (1988) "Glucosphingolipids as Sites of Action in the Chemotherapy of Cancer".

*Primary Examiner*—Jerome D. Goldberg
*Attorney, Agent, or Firm*—Harness, Dickey & Pierce

[57] ABSTRACT

An inhibitor of glycosphingolipid metabolism is used as a chemotherapeutic agent against cancer or to treat other conditions caused by cell proliferation sensitive glycosphingolipid metabolism inhibition. A preferred inhibitor is 1-phenyl-2-acylamino-3-morpholino-1-propanol.

3 Claims, No Drawings

METHOD OF CHEMOTHERAPY USING 1-PHENYL-2-DECANOYLAMINO-3-MORPHOLINO-1-PROPANOL

This invention was made with Government support under HD-07406 and NS-03192 awarded by the National Institutes of Health. The Government has certain rights in the invention.

BACKGROUND OF THE INVENTION

This invention relates generally to a method of cancer therapy sensitive to glycosphingolipid metabolism inhibition and, more particularly, to a chemotherapeutic method of treating cancer sensitive to glycosphingolipid metabolism inhibition by interfering with the metabolism of glycosphingolipids.

Sphingolipids are naturally occurring lipids in which the primary moiety is a long chain base, most commonly sphingosine. The long chain base consists of a fatty alkyl chain possessing a primary amine group at the C-2 position and two hydroxyl groups on the adjacent carbon atoms. While free sphingosine occurs at very low concentrations, most sphingosine molecules occur as amides, in which a long chain fatty acid is bound to the amino group of the base. The amides are called ceramides which serve as the metabolic precursor of all the complex sphingolipids and occur in tissues in readily detectable concentrations.

Ceramides possess a primary alcohol group at the terminal end of the long chain base (C-1 position) and a secondary alcohol group at the C-3 position. The secondary alcohol group is a free hydroxyl group in all known sphingolipids while the primary hydroxyl, in mammalian ceramide derivatives, is found bound in a beta-glycosidic linkage to a carbohydrate moiety or in an ester linkage to a phosphate moiety. The present invention is concerned with the former type of ceramide derivatives which are called glycosphingolipids.

The carbohydrate moiety that is directly attached in the glycosidic linkage in glycosphingolipids is either D-galactose or D-glucose. If only one sugar group is attached, the compound is called a cerebroside. More recently, cerebrosides have been more specifically termed glucosylceramides or galactosylceramides, depending upon their sugar moiety. The latter is found primarily in the nervous system, while the former appears to occur in all types of cells. The present invention deals particularly with glucosylceramide and its derivatives, hereinafter collectively referred to as "glucolipids".

Glucosylceramide occurs to some extent as a derivative in which D-galactose is linked in glycosidic linkage to the glucose; the derivative is called lactosylceramide or lactoside. Other glucolipids are formed from lactosylceramide by the sequential addition of other sugars, such as sialic acid, galactose, acetylglucosamine, acetylgalactosamine, and fucose. The products appear in the literature under nonsystematic names, such as globoside, hematoside, blood group substances, fucolipids, and gangliosides.

Because of the variety of linkages characteristic of sugars and the variety of enzymes responsible for linking them to one another, many different glucolipids occur in mammalian tissues. Most of these lipids are electrostatically neutral; however, the ones containing sialic acid, called gangliosides, can possess one or more negative charges, depending on the number of sialic acid moieties present. This type of glucolipid occurs in the grey matter of the nervous system at a relatively high concentration, but every type of cell contains a small amount of several types of gangliosides.

While the glucolipids have been known for many years, their low concentrations, lack of an easily quantitated group, and variety of structures have made them difficult to characterize and study. Hence, until recently, their existence and function have tended to be underplayed. However, more recently, there has been a growing recognition of the vital roles played by glucolipids in life processes. In addition to being important membrane components in animal cells, glucolipids appear to be intimately involved in tissue immunity and cell-to-cell recognition. Glucolipids, for example, mediate cell-to-cell recognition and communication by acting as distinguishing markers for cells from various organs of an animal. In addition, since the expression of glucolipids on the cell surface changes as the cell divides and differentiates, glucolipids may also be essential for the systematic growth and development of organisms.

The importance of glycosphingolipid metabolism is underscored by the seriousness of disorders resulting from defects in glycosphingolipid metabolism. For example, Tay-Sachs, Gaucher's, and Fabry's diseases, resulting from enzymatic defects in the glycosphingolipid degradative pathway and the accumulation of glycosphingolipids in the patient, all have severe clinical manifestations. Even more importantly, there is a growing body of evidence implicating glycosphingolipids, in particular, the glucolipids, in the cancer process.

For example, glucolipids have been implicated in the binding of cells to cementing proteins, such as fibronectin, and may therefore be involved in the penetrating, metastatic properties of cancer cells. They have also been found to occur as vital components of cell surface receptor sites which bind complex compounds, such as growth promoting factors which may be important in the runaway growth of cancer cells. Additionally, the glucolipid composition of cultured cells changes when the cells are infected with a virus or induced to multiply rapidly. Gangliosides have produced marked proliferation or growth of cells in vitro and in vivo.

Cancer cells also seem to have a high rate of metabolic activity of the glucolipids. Human leukemic cells have been found to have triple the normal level of glucosidase, the glucosylceramide degradative enzyme. Studies have shown ten times the normal specific activity of glycosphingolipid glactosyltransferase in a rathepatoma. A human tumor was also found to contain a glucolipid-forming enzyme, an acetylglucosamine transferase, foreign to normal cells.

The injection of glucosylceramide into mice has been shown to produce marked, rapid stimulation of the growth of the liver (which preferentially absorbs the lipid). In the case of mice bearing Ehrlich ascites carcinoma cells, the injection of glucosylceramide resulted in a greater than 50% increase in the number of cancer cells. Recent studies have also indicated that patients with Gaucher's disease, which results from an accumulation of glucosylceramide, have an unexpectedly high incidence of leukemia and other B-cell proliferation disorders.

Tumors, as they progress from slightly malignant to intensely malignant, exhibit marked changes in their assortment of glucolipids. These glucolipids from tumors have been found to interfere with the ability of lymphocytes to proliferate. This may explain the lack of effectiveness of the cancer patient's immunological protection mechanisms. However, the injection of antibodies against specific glucolipids (prepared in mice) has proved very effective in patients with melanoma.

Significantly, researchers have been finding glucolipids in tumors which do not occur in the tissue of origin (although the lipids may occur to a small extend in other normal tissues). At an accelerating pace, scientists have been finding that some of the glucolipids have never been seen before in any normal tissue. In other words, it appears that many or all tumors have the ability to produce or to accumulate new glucolipids, normally foreign to human beings. It is also important to note that all of these substances are glucolipids formed enzymatically from glucosylceramide.

A significant body of evidence shows that glycosphingolipids, in particular, glucosylceramide and its derivatives, i.e. glucolipids, play an important role in controlling the proliferation and metastasis of at least certain types of cancerous cells. This indicates that cancer cells may be peculiarly sensitive to interference with glycosphingolipid metabolism. Thus, an object of the present invention is to provide a method of chemotherapeutic treatment of cancer sensitive to glycosphingolipid metabolism inhibition by interfering with glycosphingolipid metabolism. A further object of the present invention is to provide a method of chemotherapeutic treatment of non-malignant conditions caused by uncontrolled cell proliferation such as, for example, benign tumors.

SUMMARY OF THE INVENTION

The present invention provides a method for treating cancer cells sensitive to glycosphingolipid metabolism inhibition by contacting the cells with an inhibitor in an amount effective to have a substantial inhibitory effect on glycosphingolipid metabolism. Preferably the inhibitor is a compound of the following generic formula, and therapeutically acceptable salts thereof:

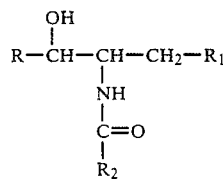

where
R is an aromatic ring, a cyclohexane, or an aliphatic group having 10 to 15 carbon atoms;
$R_1$ is an amine group; and
$R_2$ is an aliphatic group having 9 to 17 carbon atoms.
More preferably,
R is phenyl;
$R_1$ is a morpholino group;
$R_2$ is a n-nonyl chain, and the inhibitor is 1-phenyl-2-acylamino-3-morpholino-1-propanol.

DESCRIPTION OF THE INVENTION

In accordance with the present invention, cancer cells sensitive to glycosphingolipid metabolism inhibition are treated by contacting the cells with an inhibitor which interferes with the metabolic pathways of glycosphingolipids. The inhibitor can function by blocking the enzymatic synthesis of glycosphingolipids, particularly glucosylceramide and its derivatives, hereinafter collectively referred to as "glucolipids," or by blocking other physiological processing thereof such as their transport.

In addition, the method of the present invention can be used to treat non-malignant conditions caused by cell proliferation such as benign tumors, warts, skin growths and the like. The method of the present invention may also be used to prevent fetal development and terminate undesired pregnancies.

Suitable inhibitors for the practice of the method of the present invention are compounds having the following general formula, and therapeutically acceptable salts thereof:

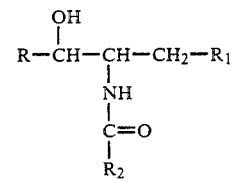

where
R is an aromatic ring, a cyclohexane, or an aliphatic group having 10 to 15 carbon atoms;
$R_1$ is an amine group; and
$R_2$ is an aliphatic group having 9 to 17 carbon atoms.

The inhibitor of the present invention can be employed in a wide variety of pharmaceutical forms; the agent can be employed neat or admixed with a pharmaceutically acceptable carrier or other excipients or additives. Generally speaking, the agent will be administered parenterally or intravenously. The selection of dosage, rate/frequency and means of administration is well within the skill of the artisan and may be left to the sound medical judgment of the treating physician or attending veterinarian. The method of the present invention may be employed alone or in conjunction with other therapeutic regimens.

Synthesis of suitable inhibitors is well within the skill of the artisan. For example, see Inokuchi and Radin, "Preparation of 1-Phenyl-2-Decanoylamino-3-Morpholino-1-Propanol," J. Lipid Research 28:565–571 (1987). Further understanding of the present invention will be had from the following experimental data.

EXPERIMENTAL DATA

Experiment 1

Male mice of the ICR (Swiss Hsd) strain from Harlan—Sprague Dawley (Indianapolis, Ind.) were injected intraperitoneal with saline containing $2 \times 10^6$ Ehrlich ascites tumor cells (EATC) on day 0. Each cage contained 4 or 5 mice which had been weight matched by a computer program for similar means (about 25 g) and similar standard deviations. Treatment began 24 hours later with intraperitoneal injections of saline or inhibitor, either as the acetate salt or as the hydrochloride salt. The inhibitor was dissolved in 40° C. saline and injected at 10 μl/g body weight. In the case of drugs that were difficult to dissolve, e.g. the hydrochlorides, a non-ionic, low toxicity detergent was included to emulsify the drug, making it suitable for injection. Two cages of mice were assigned to each control or experimental group and fed standard lab chow. In almost all cases, the mice were injected daily for a total of 10 doses.

The 1-tailed Student t-test for unpaired samples was used for statistical analysis. Table 1 sets forth the experimental results.

TABLE 1

ANTITUMOR ACTIVITY OF D-threo-PDMP (ACETATE SALT) IN MICE

| Dosage (mg/kg/day) | Surviving at 10 days (a) | Body Weight change (b) | Surviving at 60 days (c) | Surviving at 90 days (c) |
|---|---|---|---|---|
| Saline controls | 10/10 | +10.9 g | 0 | 0 |
| 1 × 100, days 1–10 | 10/10 | +1.62 | 7 (4) | 4* (4) |
| 2 × 100, days 1–5 | 10/10 | +3.78 | 5 (3) | 3* (3) |
| 1 × 150, days 1–10 | 10/10 | −0.36 | 7 (3) | 5 (3) |
| 2 × 250, days 1–5 | | | | |
| 1 × 150, days 6–10 | 8/9 | −3.49 | 5 (3) | 5 (3) |

*The mice with solid tumors were killed before 90 days to reduce suffering.

Column (a) indicates the low drug toxicity. Column (b), which shows the change in mean body weight at the end of 10 days, indicates the drug toxicity as evidenced by subnormal weight gain. Normal, uninoculated mice gain about 4.5 g during this period. The weight gain by control mice is high due to growth of EATC. Columns (c) show the number of cured mice in parentheses; the other numbers include cured mice and mice bearing a solid tumor.

The saline-injected controls consistently showed rapid formation of EATC and ascites fluid, with markedly distended abdomens (median survival about 24 days). About 30% of the mice treated with D-threo-PDMP were completely cured with a variety of regimens. Cured mice showed no signs of ascites fluid formation at any time and after 10 months, looked healthy although weight gain was temporarily slow or negative. The remaining mice died from a solid tumor version of the cells, but somewhat later than the untreated mice. The median T/C ratios for the drug were 191%, 238%, 319% and 150% for the four treated groups listed above, well above the accepted minimal values for a "highly promising" antineoplastic agent.

A dose response test of D-threo-PDMP showed that the T/C index increased with increasing dosage, as did the percentage of total cure. All animals injected with 25 or 50 mg/kg died at about the same time as the controls, although the drug reduced the chance of early death. The percentages surviving for 60 days were 10%, 20% and 50% for 75, 100, and 125 mg/kg, respectively. After more than 5 months after inoculation, 40% of the two most-heavily dosed mouse groups were still alive and healthy.

Experiment 2

The experimental procedure set forth above was again followed with homologs of PDMP made from fatty acids of 10 to 18 carbon atom length. The compounds were not resolved into D- and L-forms but the threo stereomers were used as the hydrochlorides. All samples were emulsified in Myrj 52 (15 mg/kg). Ten daily injections were given in the case of the $C_{10,12,14,18}$ homologs but the palmitoyl homolog was considered too toxic to be used more than six times. In the case of the stearoyl compound, the dosage was reduced on days 2–10 to one-half the initial level due to a high initial weight loss. The experimental results are set forth in Table 2.

TABLE 2

ANTICANCER ACTIVITY OF DL-PDMP HOMOLOGS INJECTED DAILY IN MYRJ EMULSION

| Fatty acid length | Survival after 10 days | Body Weight Increase at the 10-day point | 50-day cure | Solid Tumors at 50 days |
|---|---|---|---|---|
| Saline controls | 7/8* | 10.4 g | 0 | 2** |
| Myrj controls | 8/8 | 12.6 | 0 | 0 |
| 10 | 8/8 | 0.4 | 5 | 1 |
| 12 | 6/8 | −0.1 | 2 | 2 |
| 14 | 6/8 | 0.1 | 1 | 4 |
| 16 | 5/8 | −1.1 | 3 | 1 |
| 18 | 7/8 | 2.5 | 6 | 0 |

The drugs were injected at 0.3 mmol/kg (except for $C_{16}$ 0.15 mmol/kg and $C_{18}$ 0.15 mmol/kg on day 1 and 0.075 mmol/kg the remaining 9 days).
*One control died from the tumor before 10 days.
**Two controls lived an unusually long time, long enough for solid tumors to form.

Table 2 shows that all homologs had some therapeutic effect, with one to six normal-appearing, apparently cured mice, but that the longer chain homologs were toxic at the dosage given. The long-term cure rate with DL-PDMP was 50% at a dosage of 128 mg/kg, better than in previous studies with D-PDMP (Table). The data from the $C_{18}$ homolog show absence of an acute, initial toxicity reaction, good weight gain, and effectiveness at a lower molar dose size, compared to PDMP. It should be noted that two mice in the decanoyl group developed small solid tumors that were later resorbed apparently because the mice formed antibodies to EATC that were effective against the solid tumors, via the blood stream. This effect is to be expected for an inhibitor of glucolipid metabolism and subsequent enhancement of the host's anticancer immunodefense system.

Experiment 3

The above experimental procedures were again followed with the results set forth in Table 3.

TABLE 3

DOSE RESPONSE TEST WITH EATC AND 10 DAYS OF THE L-THREO ISOMER OF PDMP

| Dosage (mg/kg) | Weight Change after 10 days | Normal at 60 days - # of mice | Solid tumors at 60 days - # of mice |
|---|---|---|---|
| Saline controls | 13.2 g | 0 | 0 |
| 75 | 3.2 | 4 | 2 |
| 100 | 1.9 | 4 | 3 |
| 125 | 0.8 | 2 | 3 |
| 150 | −0.2 | 5 | 3 |

Although L-threo-PDMP is ineffective as an inhibitor of ceramide glucosyltransferase, and therefore could not block enzymatic formation of glucosylceramide, hereinafter designated "GlcCer," the data of Table 3 covering a 60-day observation period show that the L-enantiomer was more effective in curing the tumors than the D-enantiomer. At no time was ascites fluid visible in the treated mice, although solid tumors did develop eventually in some. The acute toxicity reactions of the mice were distinctly smaller than with the D-isomer and no losses of animals were evident during the initial 10 days of treatment. The disappearance of solid tumors was observed in two mice at the higher dosages. The effectiveness of the L-threo isomer of PDMP may be due to an inhibitory action on the galactosyltransferase that normally converts GlcCer to lactosylceramide, or to blockage of a glucolipid transfer protein.

Experiment 4

Ten normal, noncancerous mice were injected with D-threo-PDMP daily for 10 days, then killed 5 hours later with the results set forth in Table 4.

TABLE 4
TOXICITY TEST WITH D-threo-PDMP INJECTED 10 TIMES AT 100 MG/KG/DAY

|  | Controls | PDMP |
|---|---|---|
| Body Weight (g) | 28.8 (1.4) | 26.5 (1.2)** |
| Liver Weight (g) | 1.61 (0.11) | 1.32 (0.12)** |
| Liver Weight (% of body) | 5.57 (0.24) | 4.97 (0.52)** |
| Kidney Weight (g) | 0.394 (0.045) | 0.329 (0.027)** |
| Kidney Weight (% of body) | 1.37 (0.11) | 1.24 (0.13)* |
| Brain Weight (g) | 0.465 (0.025) | 0.444 (0.015)* |
| Brain Weight (% of body) | 1.61 (0.08) | 1.67 (0.08) |
| Spleen Weight (g) | 0.099 (0.018) | 0.095 (0.019) |
| Spleen Weight (% of body) | 0.34 (0.05) | 0.36 (0.07) |

Numbers in parentheses are the standard deviations. The initial mean body weights were 24.4 g.
*p is less tha 0.025.
**p is less than 0.05.

The control mice gained an average of 4.5 g while the treated mice gained 2.1 g. The treated mice had distinctly smaller weights: 8% in bodies, 18% in livers, and 17% in kidneys. The spleens were slightly but not significantly smaller and the brains were 4.6% smaller (p less than 0.025). Using the data for percent of body weight, to minimize the importance of general toxicity, only the livers and kidneys were significantly smaller (p less than 0.05%). The above decreases in organ size were in the direction expected from a diminished level of tissue glucosylceramide, since injection of the latter produced liver growth.

Experiment 5

The preceding experiment was repeated in order to observe less evanescent responses: the mice were killed 40 hours after the last injection following 12 daily injections. Here, of the absolute weights, only the kidneys were statistically different in treated mice, 11% smaller (p less than 0.05%). Comparing the 40 hour and 5 hour experiments it seems likely that the liver weights renormalized faster than the kidneys, perhaps a reflection of faster glucolipid turnover.

Cell counts made on orbital blood showed no abnormalities in RBC, WBC, differential monocytes, lymphocytes, eosinophiles, and neutrophils. This failure to harm the bone marrow and related systems compares favorably with the high toxicity of many antineoplastics.

Experiment 6

A suspension of GlcCer was injected into one group of 10 mice inoculated 1 day earlier with EATC as before. Injectable suspensions of GlcCer and galactosylceramide (GalCer) were prepared by mechanical grinding in saline (10 mg/ml) and injected at a dosage of 100 mg/kg. In one experiment, the mice were killed 1 day after the last of eight daily injections and the ascites cells were flushed out of the abdomen with buffered saline and washed. The saline-injected controls yielded 3.07 ml of packed, centrifuged cells (mean value per mouse), while the GlcCer-injected mice yielded 4.68 ml, an increase of 52% (p is less than 0.05). Cell counts with a hemacytometer showed a similar increase so it can be concluded that the cells increased in number rather than in size. Mice treated with D-threo-PDMP and GlcCer yielded 1.57 ml of cells (a 66% decrease compared with the GlcCer cells). This statistically significant difference demonstrates the ability of PDMP to inhibit EATC growth even in the presence of GlcCer.

Thus, the evidence indicates that GlcCer metabolism is a rate-limiting factor in EATC growth. In the above experiment, the rate of exogenous GlcCer uptake and utilization was not rapid enough to supply all the demands of EATC for this lipid.

Experiment 7

Treatments were begun 3 days after EATC inoculation. Only 5 injections were given and the mice were killed 1 day later. The results are as set forth in Table 5.

TABLE 5
GROWTH OF EHRLICH ASCITES CELLS IN VIVO IN THE PRESENCE OF CEREBROSIDES AND GLUCOSYLTRANSFERASE INHIBITOR

| Treatment | Volume of packed cells (ml/mouse)K | % of controls |
|---|---|---|
| Saline controls | 2.72 ± 0.95 | 100 |
| GlcCer (100 mg/kg) | 4.13 ± 0.63 | 152** |
| GalCer (100 mg/kg) | 2.29 ± 1.21 | 84 |
| GlcCer + D-threo-PDMP (100 mg/kg) | 1.40 ± 1.19 | 51* |
| D-threo-PDMP | 1.68 ± 0.86 | 62* |

*p is less than 0.05 compared with controls.
**p is less than 0.01 compared wtih controls.

As shown above GalCer showed no stimulation of EATC growth. The two lipids are catabolized to ceramide, sphingosine, and fatty acid, but only the GlcCer is anabolized to the higher glucolipids, including the gangliosides. It is important to note that the EATC absorbed both GalCer and GlcCer, as shown by thin-layer chromatography. Normal mice injected with GlcCer did not show the formation of significant numbers of free peritoneal cells.

Experiment 8

Evidence that D-threo-PDMP acts to inhibit GlcCer biosynthesis was provided as follows from assay of glucosyltransferase. Microsomes as source of enzyme were prepared by highspeed centrifugation and stored at $-70°$ C. before use. The incubations were at $37°$ C. for 30 minutes with microsomes, ATP, liposomal octanoyl sphingosine, UDP-[$^3$H]glu, $Mg^{2+}$, and dithioerythritol. Microsomes from EATC (0.50 mg protein) required 20 $\mu$M PDMP to reduce the glucosyltransferase activity in half. The microsomes from normal liver (72 $\mu$g protein) required 5 $\mu$M D-threo-PDMP. While the EATC enzyme seems to be less sensitive to the inhibitor, the intraperitoneal concentration of inhibitor is initially very high. The L-enantiomer of PDMP did not inhibit the EATC enzyme, as observed for normal mouse tissue.

Unexpectedly, it was found that glucosyltransferase specific activity in the microsomal fraction of EATC (0.41 mmol/h/mg protein) was only 1/7 that of liver microsomes from normal ICR Swiss mice. Our tentative conclusion is that these cells obtain much of their GlcCer from the peritoneum. Thus, the effectiveness of the drug can tentatively be ascribed to a blockage of GlcCer synthesis by both the host and tumor cells.

Experiment 9

Four mice who had survived 63 days post-inoculation were challenged with another $2 \times 10^6$ EATC. These mice showed no effects of the reinoculation for greater than 7 months more. Five other survivors were challenged 135 and 100 days after inoculation and four of them developed no EATC for greater than 5 months of observation. Normal mice of this age, like the younger ones, are readily attacked by EATC. We conclude that the mice have, in effect, been "live-cell vaccinated" with EATC plus PDMP.

Experiment 10

Four groups of mice (8 per group) were injected once a day for 10 d with 120 mg/kg of D-threo-PDMP and 60 or 180 mg/kg of Myrj 52 or Pluronic F68. No deaths occurred in these mice by 10 days and, at 60 days, the number of apparently cured mice was 2 and 3 for the two Myrj groups and 1 and 3 for the two Pluronic groups. The effectiveness of PDMP was clearly enhanced by the detergents at high dosages.

Since many of the glucolipids are known to exist in the outer (plasma) membrane of cells, it seems likely that the expected decrease in their concentration rendered the tumor plasma membranes physically unstable.

It should be appreciated that a latitude of modification, change and substitution is intended in the foregoing disclosure and, in certain instances, some features of the invention will be employed without a corresponding use of other features. Accordingly, it is appropriate that the appended claims be construed broadly and in a manner consistent with the spirit and the scope of the invention herein.

What is claimed is:

1. A method of treating mammalian cancer cells sensitive to glycosphingolipid metabolism inhibition by an inhibitor selected from the group set forth below, said method comprising the step of administering to the mammal a therapeutically effective amount of a composition comprising said inhibitor to retard proliferation of said cancer cells, wherein said inhibitor is selected from the group consisting of: D-, L-, and DL-threo-1-phenyl-2-decanoylamino-3-morpholino-1-propanol and therapeutically acceptable salts thereof.

2. A method of treating a mammal having a tumor sensitive to inhibition of glycosphingolipid metabolism by an inhibitor selected from the group set forth below, said method comprising the step of administering to the mammal a therapeutically effective amount of a composition comprising said inhibitor to inhibit growth of said tumor, wherein said glycosphingolipid is glucosylceramide or a functionally equivalent derivative thereof, wherein said inhibitor is selected from the group consisting of D-, L-, DL-threo-1-phenyl-2-decanoylamino-3-morpholino-1-propanol and therapeutically acceptable salts thereof.

3. A method of treating cancer cells sensitive to inhibition of glycosphingolipid metabolism by an inhibitor set forth below in a mammal, said method comprising the step of administering to the mammal a therapeutically effective amount of a composition comprising said inhibitor to retard the proliferation of said cells, wherein said inhibitor is 1-phenyl-2-decanoylamino-3-morpholino-1-propanol or therapeutically acceptable salts thereof.

* * * * *

UNITED STATES PATENT AND TRADEMARK OFFICE
CERTIFICATE OF CORRECTION

PATENT NO. : 5,041,441

DATED : August 20, 1991

INVENTOR(S) : Norman S. Radin and Jin-ichi Inokuchi

It is certified that error appears in the above-identified patent and that said Letters Patent is hereby corrected as shown below:

On the title page, item [56] References Cited:

Under the section entitled PUBLICATIONS, line 9, "F. Felding-Haberman," should be --B. Felding-Haberman--.

Column 2, line 50, "glactosyltransferase" should be --galactosyltransferase--.

Column 5, line 18, "2 x 250," should be --2 x 150,--.

Column 6, line 24, "(Table)" should be --(Table 1)--.

Signed and Sealed this

Twenty-fifth Day of May, 1993

Attest:

MICHAEL K. KIRK

*Attesting Officer*  Acting Commissioner of Patents and Trademarks

UNITED STATES PATENT AND TRADEMARK OFFICE
CERTIFICATE OF CORRECTION

PATENT NO. : 5,041,441
DATED : August 20, 1991
INVENTOR(S) : Norman S. Radin and Jin-ichi Inokuchi It is certified that error appears in the above-identified patent and that said Letters Patent is hereby corrected as shown below:

Title Page: Publications: Reference #3: "*FASB Journal*" should be --*FASEB Journal*--.

Title Page: Publications: Reference #14: "Radin et al.," should be --N.S. Radin and J. Inokuchi--.

Title Page: Abstract, line 3: "sensitive glycosphingolipid" should be --sensitive to glycosphingolipid--.

Column 2, line 50, "ra-thepatoma" should be --rat hepatoma--.

Column 4, line 53, "intraperitoneal" should be --intraperitoneally--.

Signed and Sealed this

Twenty-ninth Day of June, 1993

Attest:

MICHAEL K. KIRK

*Attesting Officer*      *Acting Commissioner of Patents and Trademarks*